United States Patent
Myoi et al.

(10) Patent No.: US 6,821,916 B2
(45) Date of Patent: Nov. 23, 2004

(54) CERAMICS FOR IN VIVO USE

(75) Inventors: Akira Myoi, Toyonaka (JP); Kohichi Imura, Zama (JP); Tomoyuki Sugiyama, Hadano (JP)

(73) Assignees: Akira Myoi, Toyonaka (JP); MMT Co., Ltd., Osaka-Prefecture (JP); Toshiba Ceramics Co., Ltd., Tokyo (JP)

(*) Notice: Subject to any disclaimer, the term of this patent is extended or adjusted under 35 U.S.C. 154(b) by 0 days.

(21) Appl. No.: 10/242,423

(22) Filed: Sep. 13, 2002

(65) Prior Publication Data

US 2003/0050171 A1 Mar. 13, 2003

(30) Foreign Application Priority Data

Sep. 13, 2001 (JP) .......................................... 2001-277798

(51) Int. Cl.[7] .......................... A61K 6/033; A61L 27/12; A61L 27/56; C04B 35/447; C04B 38/00
(52) U.S. Cl. .............................. 501/1; 501/80; 106/35; 623/23.56
(58) Field of Search ..................... 501/80, 1; 623/23.56; 106/35

(56) References Cited

U.S. PATENT DOCUMENTS

| | | | |
|---|---|---|---|
| 4,654,314 A | * 3/1987 | Takagi et al. | ................ 501/82 |
| 5,064,436 A | * 11/1991 | Ogiso et al. | ............. 623/23.56 |
| 5,866,155 A | 2/1999 | Laurencin et al. | |
| 6,340,648 B1 | * 1/2002 | Imura et al. | ................ 501/80 |
| 2002/0114938 A1 | * 8/2002 | Matsumoto | .............. 428/307.3 |

FOREIGN PATENT DOCUMENTS

| | | |
|---|---|---|
| DE | 100 18 394 A1 | 12/2000 |
| FR | 2 744 020 A1 | 8/1997 |
| JP | 4-77609 | 12/1992 |
| WO | WO 93/04013 | 3/1993 |
| WO | WO 98/15505 | 4/1998 |

OTHER PUBLICATIONS

Patent Abstracts of Japan, JP 2000–302567, Oct. 31, 2000.

* cited by examiner

*Primary Examiner*—C. Melissa Koslow
(74) *Attorney, Agent, or Firm*—Foley & Lardner LLP

(57) ABSTRACT

The invention is intended to introduce cells easily into a ceramics for in vivo use. Also, the invention provides a ceramics for in vivo use which has a good affinity to a living body and no harmful action on a living body. The invention relates to a porous ceramics having many almost globular pores and made of a component comprising a calcium phosphate type. These pores are brought into contact and communicated with each other to thereby exhibit permeability. The permeability was designed to be 150 centidarcy or more and 8000 centidarcy or less.

5 Claims, 1 Drawing Sheet

CERAMICS FOR IN VIVO USE

BACKGROUND OF THE INVENTION

1. Field of the Invention

The present invention relates to a porous calcium phosphate type ceramics, and, particularly, to a ceramics for in vivo use such as artificial bones, fillers for bones and cell culture supports, which is suitable for the purpose intended to fix and support cells and to allow these cells to grow and to be cultured.

2. Description of the Related Art

A calcium phosphate type ceramics has no harmful action on a living body and a tendency to replace for natural bones. It is therefore a preferable material as artificial bones.

However, a current calcium phosphate type ceramics used for artificial bones has large strength but involves a difficulty in fixing cells in the case where it is produced as a densified body. Also, when it is produced as a porous body, it allows cells to enter it, but it has less strength and therefore tends to be handled with difficulty.

As a method of applying such a calcium phosphate type ceramics, there is the idea that the strength is improved to a limited extent, and many cells are made to be fixed as early as possible and to grow proliferously to thereby promote the formation of bones by the power of the cell itself whereby intending to make an early recovery.

SUMMARY OF THE INVENTION

The present invention is preferably used in such an application method and provides a ceramics for in vivo use which allows cells to intrude thereinto easily and to be fixed easily, with the result that an early recovery and the like are expected.

First, the raw material of the calcium phosphate type meant in the present invention is preferably, although not particularly limited to, any one of hydroxyapatite, apatite carbonate and tricalcium phosphate or mixtures of two or more of these compounds or those containing one or more of these compounds as main component. Also, the tricalcium phosphate is preferably those having a β-phase in view of strength.

According to a first aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability and the permeability is 150 centidarcy or more and 8000 centidarcy or less.

According to a second aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability and the volume of the pores communicated with a communicating portion having a hole diameter of 8 $\mu$m or more and 20 $\mu$m or less is 2% or more and 18% or less of the volume of all pores.

According to a third aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability, the permeability is 150 centidarcy or more and 8000 centidarcy or less and the volume of the pores communicated with a communicating portion having a hole diameter of 8 $\mu$m or more and 20 $\mu$m or less is 2% or more and 18% or less of the volume of all pores.

According to a fourth aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability and the volume of the globular pores which itself have a pore diameter of 8 $\mu$m or more and 15 $\mu$m or less is 0.5% or more and 15% or less of the volume of all pores.

According to a fifth aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability, the permeability is 150 centidarcy or more and 8000 centidarcy or less and the volume of the globular pores which itself have a diameter of 8 $\mu$m or more and 15 $\mu$m or less is 0.5% or more and 15% or less of the volume of all pores.

According to a sixth aspect of the present invention, there is provided a porous ceramics for in vivo use, the ceramics comprising a calcium phosphate type raw material and having a number of pores (having many pores) having an almost globular form, wherein these pores are in contact and are communicated with each other so that the ceramics has permeability, the permeability is 150 centidarcy or more and 8000 centidarcy or less, the volume of the pores communicated with a communicating portion having a hole diameter of 8 $\mu$m or more and 20 $\mu$m or less is 2% or more and 18% or less of the volume of all pores and the volume of the globular pores which itself have a diameter of 8 $\mu$m or more and 15 $\mu$m or less is 0.5% or more and 15% or less of the volume of all pores.

DESCRIPTION OF THE PREFFERED EMBODIMENTS

In the present invention, the permeability which can be measured relatively simply using a method which has been surely established and indicates the penetrability of gas is designed to fall in a specified range and/or each proportion of the pores having a pore diameter or communicating pore diameter falling in a specified range in all pores is designed to fall in a specified range, thereby making the ceramics suitable to the intrusion of cells such as osteogenetic cells into a material for in vivo use and making it easy to fix the intruded cells.

Figure 1:
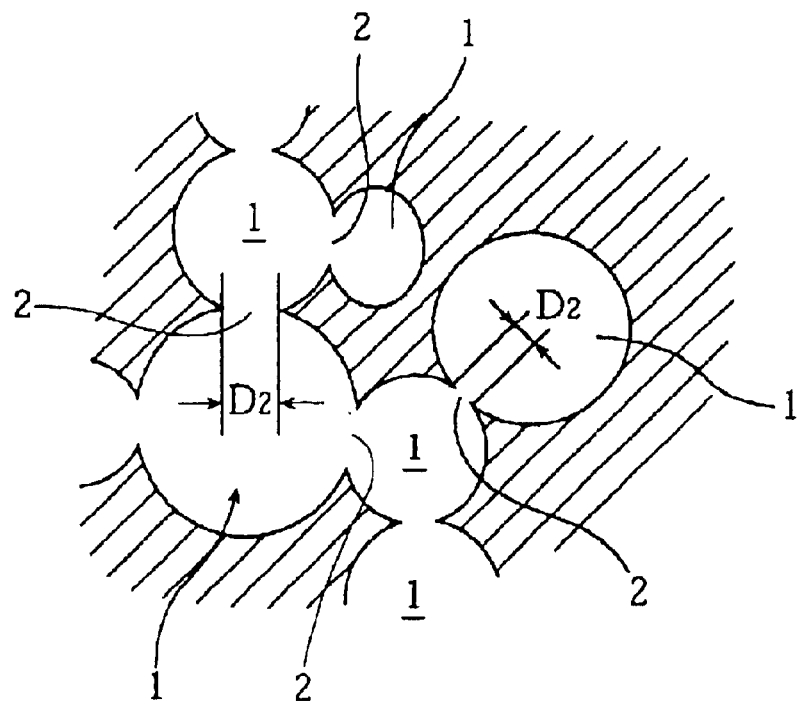
FIG. 1 is an enlarged sectional view showing one embodiment of a ceramics for in vivo use according to the present invention.

A first embodiment of the present invention will be explained. In an enlarged sectional view of FIG. 1, this ceramics for in vivo use comprises a calcium phosphate type porous sintered body, has no harmful action on a living body and has relatively high strength even if it is porous. Also, the ceramics has a good many of almost globular pores 1, in which these pores 1 are in contact among them to form a communicating portions (holes) 2. The permeability (transmittance) is designed to be 150 centidarcy or more and 8000 centidarcy or less by setting the hole diameter $D_2$ of the communicating portion (hole) 2, by selecting the number of the communicating portions.

Namely, cells are easily intruded by setting the permeability to 150 centidarcy or more. However, if the permeability exceeds 8000 centidarcy, cells are easily intruded but a problem concerning strength arises. Also, cells once intruded are not fixed and are easily flown out. The permeability is preferably 600 centidarcy or more and 5000 centidarcy or less and particularly preferably 1000 centidarcy or more and 2000 centidarcy or less.

The pore ratio is preferably 50% or more and 90% or less and particularly preferably 65% or more and 85% or less.

It is necessary that the ceramics have a proper amount of pores and moderate permeability (excessive flow is rather undesirable) to allow cells to be intruded and fixed.

In the meantime, a human cell is around 10 $\mu$m in size and the pore 1 provided with the communicating hole 2 having a size of 5 $\mu$m does not therefore contribute to the fixation of the cell. If the communicating hole 2 has a size of about 8 $\mu$m, the cells can somehow intrude into the ceramics. Although the intrusion is not easily done, the cells which intruded into the pores 1 through communication holes 2 having a diameter of as small as 8 micron ($\mu$m) or more and 20 micron ($\mu$m) or less tend to stay relatively longer than those which intruded into the pores 1 through communication holes 2 having a diameter of 20 micron ($\mu$m) or more. The inside face (inner wall surface) of the pores is formed of calcium phosphate type sintered body to which cells find easy to attach. Therefore, cells are able to stay therein for a long time such that the attachment of such cells to the inside face of the pores is prompted such that the fixation thereof within the pores tend to result.

In case where there is, particularly, a space having a size several times to tens of times the size (length dimension) of a cell, the cell strongly tends to be fixed easily. Therefore, if the range of the diameter $D_2$ of the communicating hole is designed to be around 10 $\mu$m, this is very advantageous in the fixation of the cells.

In this way, the communicating hole 2 less than 8 $\mu$m in size has a particular difficulty in the intrusion of the cells whereas if the size of the communicating hole 2 exceeds 20 $\mu$m, the cells once intruded into the pore 1 tend to flow out again. Therefore, an appropriate control during the manufacturing process such that the pores have preferable dimensions will increase the efficiency of the cell fixation there within.

It is preferable that the proportion of the volume of the pore 1 communicated with the communicating hole $D_2$ of 8 $\mu$m or more and 20 $\mu$m or less in size be 2% or more and 18% or less of the whole pore volume in terms of cumulative volume percentage. This reason is that when the proportion is less than 2%, the proportion of the hole 1 to which the cells are firmly fixed becomes too small and therefore the holes cannot contribute to the fixation of the cells, whereas when the proportion exceeds 18%, the proportion of the holes 1 into which the cells can be intruded with difficulty becomes too large (this implies that almost all the pores are associated with communicating holes having a hole diameter of 8 $\mu$m or more and 20 $\mu$m or less which is a diameter of a hole into which the cells can be inherently scarcely intruded), so that the intrusion of the cells requires more time, and also, when the proportion exceeds 18%, the quantity (proportion) of the pore 1 having a large communicating hole 2 is decreased with the result that a fluid containing nutrients and the like cannot be extended all over the whole of the calcium phosphate type sintered body. A preferable range of the proportion is 3% or more and 15% or less.

It is to be noted that the relation, meant in the present invention, between the volume of pores having a pore diameter $D_2$ of 8 $\mu$m or more and 20 $\mu$m or less and the volume of all pores, namely, the value defined in claim 2 may be found from the data measured using a mercury porosimeter.

Next, when a calcium phosphate type porous ceramics having a good many of almost globular pores 1 is made to have a structure in which these pores are in contact and are communicated with each other so that the ceramics has permeability, the permeability is 150 centidarcy or more and 8000 centidarcy or less and the volume of the pores communicated with the communicating portion 2 having 8 $\mu$m or more and 20 $\mu$m or less is 2% or more and 18% or less of the volume of all pores, the cells are easily intruded into the whole of the ceramics for in vivo use and also the cells once intruded are firmly fixed.

The ceramics for in vivo use according to the present invention is desirably an aggregate of a large number of (many) pores 1 each having a relatively uniform size and is also desirably an aggregate of the pores 1 each having a shape close to a globular form, wherein adjacent pores 1 are communicated with each other in such a manner as to allow the whole body to have permeability. The pore having an almost globular form contributes to an improvement in strength. Given as a method of the production of such a porous body are a method in which flammable globular beads and the like are added to a calcium phosphate type raw material, which is then molded under pressure and the beads are burned out during sintering and a method in which a slurry containing a calcium phosphate type raw material is made and is then stirred with controlling the viscosity of the slurry and air cells are introduced into the slurry, which is then sintered while keeping the foaming state. The latter method is preferable because the permeability is easily controllable.

Also, the pore having a communicating hole diameter $D_2$ of 8 $\mu$m or more and 20 $\mu$m or less which is a diameter of a pore in which cells are easily fixed are obtained as a globular one and the latter method is therefore preferable also in this point.

Figure 2:
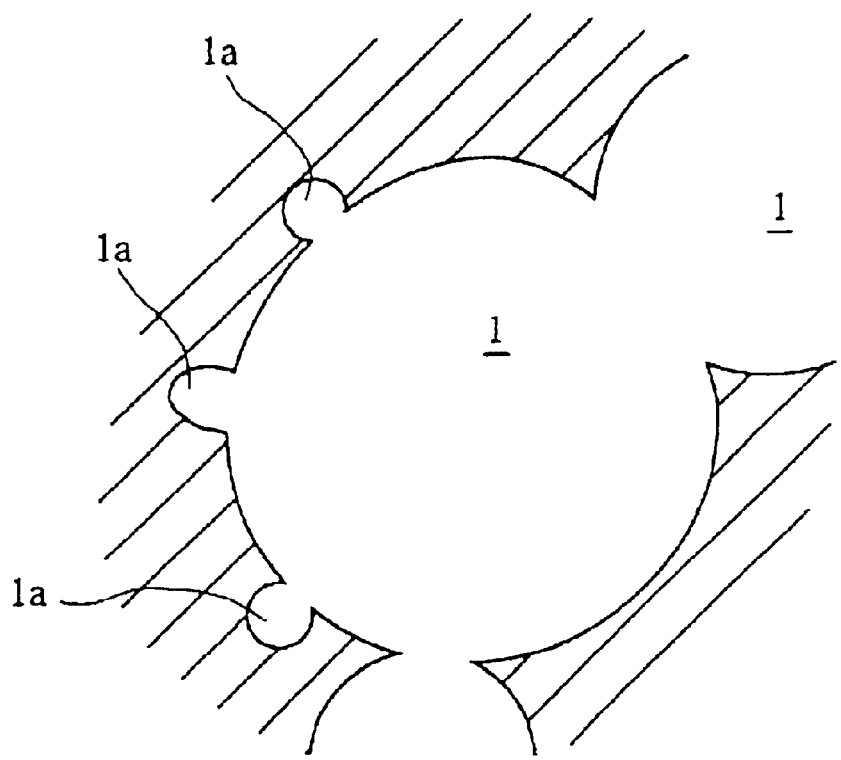
FIG. 2 is an enlarged sectional view showing another embodiment of a ceramics for in vivo use according to the present invention.

Next, another embodiment shown in FIG. 2 is a ceramics for in vivo use which has a structure in which globular pores 1$a$ each having its own diameter of 8 $\mu$m or more and 15 $\mu$m or less exist and the volume of these pores is 0.5% or more and 15% or less of the volume of the whole pores. Specifically, small pores 1$a$ are formed cavity-wise on the inner surface of a relatively large pore 1 and each own diameter of these small pores 1$a$ is 8 $\mu$m or more and 15 $\mu$m or less which is close to the size of a cell. The size of the inlet of each pore 1$a$ may be either slightly narrow or the same as the pore diameter of the pore 1$a$. A cell is tightly fitted in the pore 1$a$ and easily stabilized. Also, the pore 1$a$ faces the large pore 1. This is convenient to take in nutrients and the like. To say in other words, (plural) small pores 1$a$ are arranged small-cavity-wise on the inside peripheral surface of each of the large pores 1 and the diameter of the pore 1$a$ is set to 8 $\mu$m or more and 15 $\mu$m or less.

In the structure explained in FIG. 2, the permeability (transmittance) is preferably designed to be 150 centidarcy or more and 8000 centidarcy or less. This ensures that cells are easily intruded into the whole of the ceramics for in vivo use and the cells once intruded are firmly fixed.

The present invention is not limited to the aforementioned embodiments. The ceramics of the present invention may be either combined with other dense members or may contain active materials in the surface of the pore or the calcium phosphate type ceramics itself.

EXAMPLES

Examples 1 to 5 and Comparative Example 1

Six members (six types) for in vivo use which were produced by stirring and foaming and made of hydroxyapatite were prepared in the following production method.

First, a hydroxyapatite powder having an average particle diameter of 1 $\mu$m or less, ion exchange water which was a dispersion medium and polyethylenimide which was a cross linking polymerizable organic material were compounded in a ratio by weight of 10:8:1 and these components were mixed for 10 hours using a ball mill to prepare a slurry.

A nonionic surfactant was added to this slurry, which was then mechanically stirred to incorporate air cells into the slurry. The intensity and speed of the stirring and the amount of the surfactant to be added at this time were varied to prepare different six slurries.

An epoxy compound as a crosslinking agent was added to each slurry to be followed by stirring and then the mixture was poured into a mold. After the mixture was solidified by crosslinking polymerization and then released from the mold, followed by drying and calcinating at 1200° C.

The resulting calcined body was divided into plural products, which were then molded and thereafter washed.

Each resulting member in vivo use was measured by a mercury porosimeter to find the condition of pores and also the permeability of each member was measured according to ASTM C577-68.

Thereafter, each member was embedded in the femur of a rabbit and taken out after two weeks and six weeks respectively to observe the state of cells.

If the permeability was 150 centidarcy or more, particularly 190 centidarcy or more, cells were intruded effectively. On the other hand, members for in vivo use which had a permeability exceeding 8000 centidarcy, particularly, 10000 centidarcy were broken before and after the experiment. Although it was thought that cells are easily intruded, the members were not practical.

Comparative Examples 1 to 3

With regard to calcium phosphate type members for in vivo use which were manufactured by A company, the permeability of each member was measured, to find that each permeability was all less than 100. Also, with regard to calcium phosphate type members for in vivo use which were manufactured by B company, the permeability of each member was measured, to find that each permeability was all less than 150. Each member was embedded in the femur of a rabbit and taken out after two weeks and six weeks respectively to observe the state of cells. The quantities of fixed cells obtained after two weeks and six weeks were each one-half of those of the member of the present invention. The proportion of pores having a pore diameter of 8 $\mu$m or more and 20 $\mu$m or less to all pores was 30% or more in the case of the member of A company and 20% or more in the case of the member of B company.

With regard to the foregoing Examples 1 to 5 and Comparative Examples 1 to 3, each permeability, proportion of the volume of pores and result of the experiment (observation) are shown in the following Table 1.

TABLE 1

RESULT OF EXPERIMENT

| | Permeability (centidarcy), 1 atom, 25° C. N$_2$ gas | Proportion of the volume of pores having a communicating hole diameter of 8 $\mu$m or more and 20 $\mu$m or less to the volume of all pores (%) | Easiness of intrusion of an organization of a living body after two weeks | Formation of a myeloid tissue after 6 weeks |
|---|---|---|---|---|
| Comparative Example 1 | 10000 | 5 | Δ | Δ |
| Example 1 | 7000 | 5 | ⊚ | ⊚ |
| Example 2 | 4000 | 8 | ⊚ | ⊚ |
| Example 3 | 1300 | 10 | ○ | ○ |
| Example 4 | 650 | 10 | ○ | ○ |
| Example 5 | 190 | 13 | ○ | ○ |
| Comparative Example 2 | 100 | 24 | X | X |
| Comparative Example 3 | 50 | 35 | X | X |

⊚: Very Good
○: Good
Δ: Practical
X: Unpractical

Next, with regard to the following Example 6 and Comparative Example 4, the same experiment was made. The results of the experiment are shown in Table 2.

Example 6

One member for in vivo use which was produced by stirring and foaming in the same manner as in the above Example and made of hydroxyapitate was prepared to measure the diameters of the pores in the member. Said measurement was done by bodily embedding the member for in vivo use within the resin and subjecting the same to a microscopic observation after grinding the same. Further, the image of the pores was analyzed to correct from a two dimensional aspect to a three dimensional one in accordance with the Johnson-Saltokov method to find the ratio of the volumes of pores having a size of 8 to 15 μm. Then, the permeability of the member was measured according to ASTM C577-68.

Comparative Example 4

Also, a slurry containing hydroxyapatite was applied to an urethane foam, which was then punched by burning to obtain a sample of Comparative Example.

TABLE 2

RESULT OF EXPERIMENT

| | Permeability (centidarcy), 1 atom, 25° C. N$_2$ gas | Proportion of the volume of pores itself having a pore diameter of 8 μm or more and 15 μm or less (%) | Easiness of intrusion of an organization of a living body after two weeks | Formation of a myeloid tissue after 6 weeks |
|---|---|---|---|---|
| Example 6 | 190 | 2 | ○ | ○ |
| Comparative Example 4 | 8800 | 0.01 | Δ | Δ |

◎: Very Good
○: Good
Δ: Practical
X: Unpractical

Next, a sample (a cylindrical body having a diameter of 30 mm and a height of 10 mm formed from hydroxyapatite having a porosity of 75%) similar to one in Example 3 was subjected to measurement in the following condition: pressure difference: 620 mm H$_2$O and 24 to 34° C., to find that the amount of permeated water was 105 (cc/cm$^2$·min).

If the permeability is kept within the range of from 16 (cc/cm$^2$·min.) up to 600 (cc/cm$^2$·min.), the intrusion of liquids is facilitated such that nourishments for cells are preferably carried thereto.

It is to be noted that the permeability can be measured according to the method as described in Japanese Patent Publication No. H4-77609.

Cells can be easily introduced into the ceramics for in vivo use. It is needless to say that because a porous calcium phosphate is used as a raw material, the ceramics has a good affinity to a living body and has no harmful action on a living body.

The same effect as that of claim 1 is produced and the cells entering the ceramics for in vivo use can be fixed firmly.

Cells can be introduced and fixed rapidly.

Cells can be rapidly introduced into the ceramics for in vivo use and the cells entering the ceramics for in vivo use can be firmly fixed.

What is claimed is:

1. A calcium phosphate type porous ceramics for in vivo use, the ceramics having a number of pores having an almost globular form, wherein these pores are in contact and are communicated with each other so that the ceramics has permeability and the volume of the pores communicated with a communicating portion having a hole diameter of 8 (m or more and 20 (m or less is 2% or more and 18% or less of the volume of all pores.

2. A calcium phosphate type porous ceramics for in vivo use, the ceramics having a number of pores having an almost globular form, wherein these pores are in contact and are communicated with each other so that the ceramics has permeability, the permeability is 150 centidarcy or more and 8000 centidarcy or less and the volume of the pores communicated with a communicating portion having a hole diameter of 8 (m or more and 20 (m or less is 2% or more and 18% or less of the volume of all pores.

3. A calcium phosphate type porous ceramics for in vivo use, the ceramics having a number of pores having an almost globular form, wherein these pores are in contact and are communicated with each other so that the ceramics has permeability and the volume of the globular pores which itself have a pore diameter of 8 (m or more and 15 (m or less is 0.5% or more and 15% or less of the volume of all pores.

4. A calcium phosphate type porous ceramics for in vivo use, the ceramics having a number of pores having an almost globular form, wherein these pores are in contact and are communicated with each other so that the ceramics has permeability, the permeability is 150 centidarcy or more and 8000 centidarcy or less and the volume of the globular pores which itself have a diameter of 8 (m or more and 15 (m or less is 0.5% or more and 15% or less of the volume of all pores.

5. A calcium phosphate type porous ceramics for in vivo use, the ceramics having a number of pores having an almost globular form, wherein these pores are in contact and are communicated with each other so that the ceramics has permeability, the permeability is 150 centidarcy or more and 8000 centidarcy or less, the volume of the pores communicated with a communicating portion having a hole diameter of 8 (m or more and 20 (m or less is 2% or more and 18% or less of the volume of all pores and the volume of the globular pores which itself have a diameter of 8 (m or more and 15 (m or less is 0.5% or more and 15% or less of the volume of all pores.

* * * * *